United States Patent [19] [11] Patent Number: 4,894,452
Stephan [45] Date of Patent: Jan. 16, 1990

[54] CYANURIC ACID PRODUCTION BY CONTROLLED PYROLYSIS OF BIURET

[75] Inventor: Kurt F. Stephan, Wenatchee, Wash.

[73] Assignee: Lenroc Company, Ephrata, Wash.

[21] Appl. No.: 182,504

[22] Filed: Apr. 18, 1988

[51] Int. Cl.$^4$ .......................................... C07D 251/32
[52] U.S. Cl. .................................................. 544/192
[58] Field of Search ........................................ 544/192

[56] References Cited

U.S. PATENT DOCUMENTS

| | | | |
|---|---|---|---|
| 2,822,363 | 2/1958 | Christmann | 544/192 |
| 2,872,447 | 2/1959 | Oehlschlaeger | 544/192 |
| 2,943,088 | 6/1960 | Westfall | 544/192 |
| 2,952,679 | 9/1960 | Perret | 544/192 |
| 3,008,961 | 11/1961 | Wojcik | 544/192 |
| 3,065,233 | 11/1962 | Hopkins | 544/192 |
| 3,093,641 | 6/1963 | Formaini | 544/192 |
| 3,172,886 | 3/1965 | Christoffel et al. | 544/192 |
| 3,236,845 | 2/1966 | Baskin | 544/192 |
| 3,336,309 | 8/1967 | McBrayer | 544/192 |
| 3,563,987 | 2/1971 | Berkowitz | 544/192 |
| 3,953,443 | 4/1976 | Ohata et al. | 544/192 |
| 4,093,808 | 6/1978 | Nelson | 544/192 |
| 4,474,957 | 10/1984 | Sato et al. | 544/192 |
| 4,654,441 | 3/1987 | Stephan | 544/192 |

Primary Examiner—Richard A. Schwartz
Assistant Examiner—Robert C. Whittenbaugh
Attorney, Agent, or Firm—Graybeal, Jensen & Puntigam

[57] ABSTRACT

The process of producing from urea a reaction product which is predominantly cyanuric acid, which process involves only the application of heat without use of solvents or catalysts. The process in its first stage involves heating molten urea for a time and at a temperature to convert the urea to a first stage reaction product comprising less than 40% urea and at least 30% biuret, then cooling and comminuting the first stage reaction product, then as a second stage of the process, passing hot air through the comminuted first stage reaction product at temperatures progressively increasing but maintained below the melting point of the reaction, such solid phase heating of the reaction product during the second stage of the process being maintained until the cyanuric acid content is at least about 50% of the final reaction product and is preferably at least about 70%.

12 Claims, No Drawings

CYANURIC ACID PRODUCTION BY CONTROLLED PYROLYSIS OF BIURET

BACKGROUND OF THE INVENTION

1. Field of the Invention

This invention relates to a process for the production of cyanuric acid and more specifically to the pyrolysis of urea and its reaction products in two stages, the first stage of the reaction starting with urea in molten form and resulting in a reaction product which comprises about 30% to 60% biuret by weight, and the second stage of which involves further pyrolysis of the first stage reaction product in dry, particulate, solid form to effectively reduce the biuret content and increase the cyanuric acid content to the point of the product being predominantly, up to about 90%, cyanuric acid by weight, and solvent free.

2. Description of the Prior Art

Traditionally, cyanuric acid is produced by heating urea at temperatures between 180° C. and 300° C. according to the following reaction:

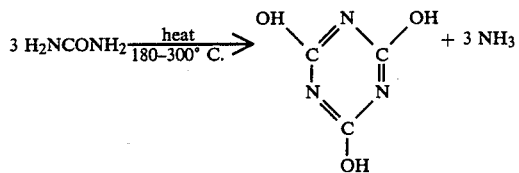

As urea decomposes, cyanuric acid as well as other pyrolysis products such as biuret, triuret, ammelide, and ammeline are formed with the reaction mass passing from a liquid state to an increasingly viscous slurry. Further heating of the material produces an extremely sticky, solid cake which adheres to equipment surfaces, is difficult to heat, and inhibits the release of ammonia. Various process routes have been used to overcome this handling problem.

Formaini U.S. Pat. No. 3,093,641 discloses a process employing a two-step reaction in which urea is first pyrolyzed to an intermediate reaction product containing about 30% to 50% unreacted urea. In the second step this material, while still molten, is applied as a thin film (less than 0.5 in. thick) to the surface of a rotating drum heated to between 200° C. and 300° C. The Formaini process does provide a means of heat transfer through the sticky, plastic state, but is limited to a rapid reaction time at temperatures above 200° C. in the second stage. The higher temperature of reaction favors the increased production of the by-product ammelide in the resultant product. Ammelide is undesirable in most cyanuric applications and must be removed via acid digestion. In addition the second stage of heating on a rotating drum is not free from problems caused by the product adhering to the equipment. Operating errors can promote major jamming of equipment with accumulated product.

Westfall U.S. Pat. No. 2,943,088 discloses a process whereby cyanuric acid is prepared by heating urea at a temperature of 240° C. to 360° C. while continuously moving it so that it melts and deammoniates through a viscous plastic state into a hard solid state to form a crude reaction product in the form of small granules consisting largely of cyanuric acid, ammelide, ammeline, and minor quantities of other impurities. This patent asserts that urea alone can be used as a feedstock or alternatively, molten urea can be blended with a crude cyanuric product (5% to 35% urea, 95% to 65% cyanuric) to obtain a free flowing mixture which can then be heated in the range of 210° C. to 375° C. to deammoniate the urea through a viscous plastic state to a hard solid state, and moving it through the heated zone while continuously agitating the blend to preserve the granules in free-flowing form. As with Formaini the temperature of reaction cited by Westfall, i.e. above 210° C., tends to generate substantial quantities of impurities, notably ammelide, in the resultant final product. Several examples given by the Westfall patent contain about 40% impurities by weight.

Both the Formaini and Westfall processes have framed the operating parameters of time and temperature, i.e. about 200° C. and up to 200 minutes, so that a very crude cyanuric product is formed. Such products require significant acid digestion to obtain a pure cyanuric acid. Ammelide is an impurity that becomes particularly troublesome in that its chemical structure is similar to cyanuric acid, requiring sophisticated analytical techniques to distinguish between the two. Also, the manufacture of chlorinated isocyanurate products requires that essentially pure cyanuric acid containing a minimum of 95% cyanuric acid be used in the chlorinated step.

Baskin U.S. Pat. No. 3,236,845 discloses a dry process wherein 7–40 parts of cyanuric acid and one part urea are fed through a reactor at 200°–300° C. by helical screw conveyor means with the pyrolysis involving 1–2 minutes transit time. Conveyance can also be by pug mill paddles with a 30 minute residence time at about 280° C.

McBrayer U.S. Pat. No. 3,336,309 discloses a process involving agitating and heating of urea to 432°–450° F. and then to about 535° F.

Ohata et al U.S. Pat. No. 3,953,443 involves agitating and heating of urea to greater than 340° C. and then to greater than 220° C. for over 2½ hours.

Sato et al U.S. Pat. No. 4,474,957 involves heating cyanuric acid and urea to 260°–270° C. in a kiln with cyanuric acid product recycling.

The present discovery, which is surprising and of great economic benefit, is that reaction products comprising principally cyanuric acid can be produced by a relatively low temperature process with minimal by-product production of ammelide as an impurity, and with avoidance of the difficulty customarily expected in the handling of a intermediate urea pyrolysis product in its plastic, sticky state. Hithertofore, this has only been accomplished by suspending such intermediate product in a suitable heated liquid solvent.

There are several prior U.S. patents that disclose processes which employ an inert liquid solvent as a heating medium and suspension agent for a feedstock which may include urea, biuret, cyanuric acid, and other homologs, namely U.S. Pat. Nos. 2,822,363, to Christmann, 3,563,987, to Perret, 3,065,233, to Hopkins, 2,872,447, to Ochlschlaeger, 3,008,961, to Wojcik, 3,563,987, to Berkowitz, 3,172,886, to Christoffel, and 3,164,591 to Walles. Heat transfer and removal of evolved ammonia is very good in such systems and adhesion of product to equipment surfaces is lessened. Since the plastic phase of the reaction mass which in general corresponds to an analysis of 21% to 29% urea is overcome by dispersion in a solvent, the temperature and time of reaction in a solvent process is quite arbitrary, being in a range of 150° C. to 300° C. and generally from 1 to 10 hours. Product yields can be quite extraordinary as evidenced by the process disclosed in U.S. Pat. No. 3,563,987, to Berkowitz which asserts a purity as high as 99.7% cyanuric acid with a yield of 97%. The generation of ammelide can be reduced by using operating temperatures about 200° C. or less in combination with vacuum or a gas sweep to rapidly remove released ammonia from the reaction mass, but only at the added cost of the expensive solvent unavoidably lost in the vapor phase. Another major limitation in the solvent approach is the filtration step required to separate the cyanuric acid from the solvent. This step of necessity often generates a waste stream of such solvents as dipropylene glycol, phenols, alkylsufones, tetrahydrofurfuryl alcohol, or trichlorobenzene which must be recovered. Other problems include emission of the solvent in the ammonia offgas stream, making the ammonia unsuitable for some end uses such as a nitrogen source in fertilizers, and the breakdown of the solvent in repeated heating cycles. All of the solvents suggested also pose exposure hazards to operating personnel and require significant operating procedures for environmental and safety reasons.

U.S. Pat No. 4,093,808 to Nelson involves agitating and heating cyanuric acid with a minor amount of nitric acid or ammonium nitrate to 250°-300° C.

The prior art patents most closely related to the present invention are believed to be Stephan et al U.S. Pat. Nos. 4,540,820 and 4,654,441. These patents disclse a two step process for the production of biuret in a form suitable for use as animal feed, comprising at least 55% biuret by weight. The preparation of the feedstock, i.e. a first phase intermediate reaction product by controlled pyrolysis of urea, is generally quite similar for the feed grade biuret process and for process of the present invention, and it is to be noted that both the earlier Stephan et al biuret production process and the present process for formation of a predominantly cyanuric acid product employ a second stage of heating of a comminuted solid product in a forced air recirculating oven. Example 3 of U.S. Pat. No. 4,654,441 indicates that a product containing as much as 42.5% cyanuric acid by weight can result from the earlier process, which product, however, is not suitable for use as animal feed grade biuret. However, neither of the cited prior Stephan et al patents discloses any teaching with regard to attaining products comprising more than 50% cyanuric acid by weight, or how to effectively realize such products. The Stephan et al biuret production processes, as disclosed in the noted prior Stephan et al patents, emphasize minimal conversion of the urea and biuret to cyanuric acid and, in actual operating practice (in keeping with the FDA requirement of less than 30% cyanuric acid in animal feed grade biuret), require second stage heating at less than 130° C.

Heretofore, cyanuric acid production processes which operate without a solvent and which produce a relatively high purity cyanuric acid with minor amounts of ammelide have been difficult to attain. Prior art teachings suggest that temperatures above 200° C. are necessary for significant non-solvent conversion to cyanuric acid. Experience has shown, however, that heating of the urea/biuret Stephan et al first stage intermediate reaction product above 200° C. results in excessive production of ammelide, severe loss of product through sublimation of the urea, biuret, and other intermediates, and shrinkage of the product bed in the second stage of heating which causes uneven conversion of cyanuric acid as a result of uneven exposure of the reactants to air. What is surprising and the object of this invention is that an intermediate biuret feed stock can be converted to predominantly cyanuric acid with minor amounts of ammelide at temperatures of 200° C. or less without incurring substantial losses in sublimed product or without rendering the second stage heating of the solid comminuted product ineffective. As a practical matter, it is important to maintain the level of heating at not more than the temperature at which the comminuted second stage reactants soften, so as not to reduce reactant surface area and consequent reduction in contact thereof with heated air. As a practical matter, also, it is important, for a commercial process in which the cyanuric acid content of the reaction product is to be maximized consistent with practical production times, that the comminuted product from the first stage of urea/biuret pyrolysis be such that the urea content of the feedstock to the second stage be less than about 40% by weight and the biuret content thereof be more than about 30% by weight so that the second stage heating by heated air flow through the comminuted feedstock can proceed at an effective temperature and be progressively increased fairly rapidly without melting of the communited product bed, with higher temperatures approaching 200° C. during the latter phases of the second stage reaction being effective to maximize the cyanuric acid content of the final reaction product.

As indicated, the process of the present invention does not employ a solvent and thereby avoids the filtration step required to separate solvent and product and the environmental problems inherent in use of a solvent. Also, the ammonia offgas can be captured as a pure stream that is not contaminated with solvent vapor. The present invention still however retains the benefits of a low temperature conversion process that selectively favors the formation of cyanuric acid. The problem of adhesion of product to equipment is also totally bypassed. In this way the process of the present invention overcomes the limitations inherent with previous non-solvent processes, which involve higher levels of impurities in the course of the conversion to cyanuric acid and do not totally eliminate sticking problems, and is also an improvement over the solvent processes by eliminating the negative consequences of solvent use.

SUMMARY OF THE INVENTION

According to the present invention, a feedstock containing less than 40% urea and at least 30% biuret by weight may be converted to cyanuric acid by subjecting the feedstock in particulate form to a heat treatment in the substantially solid state with forced gas flow through the particulate reaction mass. A product results which consists of over 50% to essentially 90% cyanuric acid together with minor amounts of ammelide, ammeline, triuret, biuret, and urea, which is nevertheless free of any solvent or catalyst.

In carrying out this invention, a feedstock comprising less than 40% urea and more than 30% biuret in dry particulate form is treated in an oven with forced gas circulation at a temperature that softens but does not significantly melt the particles yet is sufficient for pyrolysis to occur. Depending on the respective amounts of biuret, urea, cyanuric acid, and triuret and other related homologs which may be found in a given feedstock, and in general, the appropriate reaction temperature will be between 100° C. and 200° C. Since the melting point of the feedstock is directly related to the percentages of urea and biuret, e.g. the lower the urea below 40% the higher the biuret above 30% the higher the melting point, the heating temperature in the oven varies both as to initial temperature and as to rate of increase in temperature, and the rate of reaction will extend to as long as 100 hours for feedstocks of low biuret analysis to as short as 1 hour for feedstocks of high biuret analysis. During this second stage of pyrolysis it is essential that the feedstock be maintained in essentially solid state with at most only incipient surface fusion (softening) of the particles, as distinguished from the molten, i.e. liquid, state, so that substantial sublimation of urea can occur as well as evolution of ammonia from the product.

A typical feedstock for this process may be prepared, for example, by reacting urea at 155° C., with an air sweep of the ammonia released, for 9 hours to give a product having an analysis by weight of urea 32%, biuret 42.1% and cyanuric acid 16.7%, cooling the autoclave product below its melting point, and comminuting it. One method of accomplishing this is to drain the molten product into trays and allow it to cool ambiently and to solidify before comminuting.

It is advantageous in carrying out the process of the invention to have the feedstock comminuted to a mesh size of from about 1 mesh to 16 mesh (i.e. where the diameter of the particles is from 1 inch to 1/16th inch, and preferably about 4 mesh (i.e. about ¼ inch in diameter) and smaller.

The comminuted feedstock is suitably placed in wire mesh trays or the like to a bed depth of between ½ inch to four feet or more, and placed in a forced air circulating oven or the like with hot air circulated either vertically or horizontally through the particulate mass in each tray. The temperature is preferably thermostatically controlled to within ±3° C. within the oven.

The comminuted feedstock is placed in or on a container porous to air, such as a tray or other box-type container with a screen or like foraminous bottom and open top, which arrangements provide what may be generically termed a fixed bed. Alternatively, the feedstock bed may be arranged on a wire screen or like foraminous conveyor, or in a fluidized chamber, which arrangements provide what may be generally termed a movable bed.

The depth of the bed of the particulate material can be any desired depth consistent with the need to maintain substantial and continuing forced gas flow in contact with the surfaces of the particulate material, and considering also that under a given operating condition a given total amount of contact of circulating gas with the surfaces of the particles is necessary to achieve the result of substantial urea sublimation and urea conversion to biuret and cyanuric, and also a major conversion of biuret to cyanuric. These considerations involve several interrelated factors such as average mesh size of the particles, the temperature of the gas, the depth of the particle bed, and the volume of hot gas flow past the particles. Thus, for example, in a situation where a fixed bed, two feet in depth, is composed of reactant particles having an average mesh size of 8 mesh, (i.e. 0.125 inch in diameter), a pressure drop of 0.16 psig per foot of bed thickness has been found satisfactory for the operating condition where the hot gas and particles are heated at a progressively increasing temperature, in the range of from 125° C. to 180° C., for 60 hours. Correspondingly, however, when the average particle size is 4 mesh, an optimized pressure drop through a bed 2 feet thick to accomplish a similar end product within the same temperature range has been found to be 0.13 psig per foot of bed and the heating should continue for a period of 80 hours.

Comminution of the solidified and broken-up pieces of the partially pyrolyzed reaction product resulting from the first stage of reaction of urea can be carried out in any appropriate mechanical disintegrater such as a jaw crusher, rotary crusher, hammermill, or the like.

The following Table I demonstrates the effect of variation in temperature on the constituency of the first stage reaction product, in the range 150° C.-200° C. in 5° increments. As will be noted, a relatively higher reaction temperature in this range results in relatively less conversion of urea to biuret and cyanuric acid in a relatively shorter time. Considering, however, that all of the reaction products reflected in the Table are satisfactory starting materials for use as the charge in the second stage of the present invention, and that a relatively lesser proportion of urea and relatively greater proportion of biuret are preferred from the point of view of the reaction taking a shorter time during the second stage of the process, the selection for commercial purposes of the reaction temperature at which the first stage of the process is to proceed is in the nature of a compromise between the time of reaction restraints during the first stage and the time of reaction restraints during the second stage.

TABLE I

Analysis Of First Stage Product That Can Be Attained At Various Temperatures During First Stage Reaction

| Temperature of Reaction - 1st Stage (Degrees C.) | 150 | 155 | 160 | 165 | 170 | 175 | 180 | 185 | 190 | 195 | 200 |
|---|---|---|---|---|---|---|---|---|---|---|---|
| Time (Hours) | 15 | 11 | 8 | 7 | 6 | 5 | 4 | 3 | 2 | 1.5 | 1 |
| Urea % | 28 | 30 | 32 | 33 | 34 | 35 | 36 | 37 | 38 | 38 | 38 |
| Cyanuric % | 14 | 16 | 18 | 20 | 22 | 24 | 26 | 27 | 28 | 29 | 30 |
| Biuret % | 52 | 49 | 46 | 44 | 42 | 40 | 38 | 35 | 32 | 31 | 29 |
| Triuret % | 6 | 5 | 4 | 3 | 2 | 1 | 0 | 0 | 0 | 0 | 0 |
| Ammelide % | 0 | 0 | 0 | 0 | 0 | 0 | 0 | 1 | 2 | 2 | 3 |
| Melting Point (Degrees C.) of 1st Stage Products Listed Above | 121 | 122 | 122 | 123 | 125 | 127 | 130 | 133 | 136 | 139 | 144 |

The following Table II demonstrates certain of the considerations involved in balancing reaction time during the first stage of the process with a desired constituency for the charge or starting material for the second stage of the process of the present invention. The data in Table II selects a given reaction temperature during the first stage of the process (155° C.) and shows the effect of reaction time on the first stage reaction product constituency. As will be noted, the urea content does not reach a usably low proportion until after about 6 hours of reaction time (40% urea) and continues to decrease with some 30% proportion of urea being reached after about 12 hours reaction time, whereas a biuret content reaches almost 40% after about 2 hours reaction time and generally levels off thereafter, remaining constant at about 47%. However, the melting point of the first stage reaction product as reflected in the data in Table II shows a pronounced eutectic in the 103° C.–106° C. range until the urea content is reduced to below 40%, following which it gradually, then more abruptly, rises to 123° C. after 12 hours reaction time. It is a practical operating parameter of the process of the present invention that the reaction product forming the starting material charge for the second stage of the process of the present invention should be of a character where the eutectic of the melting point of the product is rising, i.e. where the urea content is less than about 40%, and preferably where the melting point is substantially above the eutectic melting point, i.e. where the urea content is not more than about 30% and the biuret content is at least 40%.

TABLE II

Analysis Of First Stage Reaction Product Attainable At A Reaction Temperature of 155 C. Versus Time of Reaction

| Reaction Time (Hours) 1st Stage | 0 | 1 | 2 | 3 | 4 | 5 | 6 | 7 | 8 | 9 | 10 | 11 | 12 |
|---|---|---|---|---|---|---|---|---|---|---|---|---|---|
| Urea % | 100 | 76 | 59 | 53 | 48 | 44 | 40 | 37 | 35 | 33 | 32 | 31 | 30 |
| Biuret % | 0 | 23 | 38 | 41 | 44 | 45 | 46 | 47 | 47 | 47 | 47 | 47 | 47 |
| Cyanuric % | 0 | 0 | 2 | 4 | 6 | 8 | 10 | 12 | 14 | 16 | 17 | 18 | 19 |
| Triuret % | 0 | 1 | 1 | 2 | 2 | 3 | 4 | 4 | 4 | 4 | 4 | 4 | 4 |
| Melting Point Of The Above Products (Degrees C.) | 133 | 109 | 103 | 104 | 104 | 105 | 106 | 107 | 109 | 111 | 114 | 118 | 123 |

Since this invention is based upon a two-stage reaction, the initial stage of which is carried out at a temperature above the melting point of urea (forming a partially pyrolyzed reaction product comprising urea, cyanuric acid and biuret), the product analysis of the first stage is critical to the success of second stage, i.e. the feedstock analysis determines the starting temperature and the rate of increase of the temperature to which the particulate material is heated during the second stage. The partially reacted feedstock as used as the starting material for the solid state, second-stage pyrolyzation of the present invention may have the following ranges of constituents, with percentages given in percent by weight:

| Constituent | General Limits | Optimum Limits |
|---|---|---|
| cyanuric acid | 0–40% | 10–30% |
| biuret | 30–60% | 35–50% |
| urea | 10–40% | 25–35% |

Pyrolysis products having compositions within the foregoing ranges are obtainable, for example, by adjusting the first-stage pyrolysis variables of time, temperature and pressure to within the following limits, with time and temperature being generally inversely related:

| Parameter | General Limits | Optimum Limits |
|---|---|---|
| Time | 1–24 hrs. | 4–12 hrs. |
| Temperature | 220°–135° C. | 180°–150° C. |
| Pressure | 200–1520 mm | 760–1200 mm |

Cyanuric acid can readily be obtained by reacting the intermediate feedstock prepared in the above manner, with or without seed material addition during cooling, by adjusting the reaction variables of time, temperature and pressure to within the following limits, with time and temperature being generally inversely related:

| Parameter | General Limits | Optimum Limits |
|---|---|---|
| Time (hours) | 1–100 | 5–70 |
| Temperature (°C.) | 220–100 | 200–110 |
| Pressure (mm) | 200–1520 | 600–1000 |

The process may be carried out under atmospheric pressure or such slight negative pressure as may be required to recover the byproduct ammonia. While higher than atmospheric pressure may be used, there is no particular advantage in its use.

In a given run, when the feed material for the further pyrolysis of the product in solid form is at hand and a determination is to be made as to the temperature at which the further, second stage pyrolysis is to proceed, a sample of the feed material can be analyzed for softening point, such as by analysis on a Fisher Johns melting point detector, as marketed by the Fisher Scientific Company. During such an analysis, as the temperature of the sample is raised progressively, and as it reaches the point where the sample starts to soften, its color changes from a white dry, particulate appearance to a duller, grayish moist, shiny appearance. Further increase in temperature then causes such moist appearance to change to a glistening appearance and finally to a puddled, melted state which is definitely indicative of the melting point. The temperature at which the first change in appearance from softening occurs is the temperature at or slightly below which the final pyrolysis of the product should start. However, as the further pyrolysis reaction proceeds, and the urea content of the reaction mass is further reduced with the biuret and cyanuric content thereof progressively increasing, the softening point of the mass progressively increases because of the changing constituency of the reaction mass. The progressive increase in softening point permits a progressive increase in the temperature at which the reaction proceeds in the course of the run. A feedstock, for example, which contains 45% biuret can be initially heated at about 110° C. while a feedstock that contains 60% biuret can be heated initially to a temperature of about 160° C. without undue softening.

The final reaction product may be comminuted in a hammermill to a desired mesh size or alternatively may be ground to a sub-size and then compacted to a larger mesh size.

One object of this invention is the production of a heat stable, substantially non-melting (below 185° C.), crude mixture of biuret, triuret, cyanuric acid, ammelide, and ammeline, together with minor amounts of other pyrolysis products and a minor amount of unpyrolyzed urea which is suitable feedstock for the subsequent production of isocyanic acid (HCNO) upon further pyrolysis and which may be used to reduce the NOx content in the offgas which results from the burning of hydrocarbon fuels such as coal, diesel oil, wood chips, and the like.

DESCRIPTION OF THE PREFERRED EMBODIMENTS

EXAMPLE 1

A charge of 22,000 pounds of commercially available technical grade urea was placed in a 4,000 gallon stainless steel reactor and heated until molten and thereafter at 155° C., the total heating time being 9.5 hours. Ammonia was swept from the reactor by air supplied at 1,500 cfm standard temperature and pressure (STP) from a Gardner-Denver rotary blower. The intermediate product resulting from the initial autoclave had the following composition:

|  | % by weight |
|---|---|
| urea | 33.0 |
| biuret | 42.7 |
| cyanuric acid | 18.1 |
| other pyrolysis products | 6.2 |
|  | 100.0 |

18,480 pounds of this product, representing 84% of the initial charge of urea, was recovered and comminuted so that the resulting particles were between 4 mesh and 1 mesh (¼ inch to 1 inch) in size. 1,000 pounds of this sized material was placed in a forced air heated oven with a horizontal tray wherein the product bed depth was approximately 12 inches. 1,680 cfm (STP) was forced upwardly through the product bed at an initial temperature of 110° C. Over a 16 hour period the temperature was gradually increased to 127° C. and the charge was heated at this temperature for an additional 20 hours. At the end of this period the product bed temperature was progressively increased to 204° C. over a four hour period and heated an additional 20 hours at this temperature, the total elapsed heating time being 60 hours. 560 pounds of cyanuric acid material was recovered and had the following analysis: 0% urea, 10.0% biuret, 8.3% ammelide, and 81.7% cyanuric acid.

EXAMPLE 2

A biuret feedstock which analyzed 55% biuret, 22% cyanuric acid, 8% triuret, and 15% urea was placed as a 300 g sample in a steel pan in a convection oven at 173° C. Particle size ranged from ¼ inch diameter to ½ inch diameter. After 2 hours the product analyzed 35% cyanuric acid. The sample was cooked for an additional 2 hours at 210° C. and analyzed at 65% cyanuric acid, 28% biuret, 2% urea, and 5% ammelide. Individual particles retained their shape throughout the 4 hour cooking cycle and did not adhere to the metal pan.

EXAMPLE 3

A feedstock with an analysis as in Example 2 was sized to 10–20 mesh and 25 grams of this material were placed in a steel pan in a turbo oven for 24 hours at 138° C. The material then analyzed at 37% cyanuric acid. Material run through this identical procedure but heated at 163° C. for 24 hours analyzed 54.4% cyanuric, while material heated at 180° C. for 24 hours analyzed at 71% cyanuric. Finally, material as above heated at 204° C. for 24 hours analyzed at 86.1% cyanuric acid.

EXAMPLE 4

One thousand pounds of feedstock material which had been sized to between 1 mesh and 4 mesh was loaded into a forced air heated oven with a horizontal tray area of 16 square feet and a tray bottom composed of 3/16 opening steel screen. This feedstock analyzed as follows: urea 16.4%, cyanuric acid 25.2%, triuret 4.9%, biuret 53.5%. The bed depth of the product in the horizontal tray was 12 inches. Air at the rate of 1,680 cfm was forced upwardly through the product bed with the bed at an initial temperature of 182° C. so that the product bed temperature was taken from 24° C. at the start of heating to 132° C. at the end of a one-hour period. Thereafter the product bed temperature was gradually increased so that after 5 hours of heating the charged material was at 143° C., at 10 hours it was at 149° C., and at 15 hours it was at 160° C. The product was thereafter maintained at 160° C. for an additional 9 hours. The total time of heating in the forced air oven was 24 hours. The final product was unloaded from the oven, allowed to cool to 24° C., and ground in a Fitzpatrick hammermill so that all of the product was smaller than 16 mesh and 48% of the product was smaller than 60 mesh. 776 pounds of sized final product was recovered and had the following analysis: urea 2.3%, cyanuric acid 53.1%, triuret 2.1%, biuret 40.9%, and ammelide 1.6%.

EXAMPLE 5

A charge of 22,000 pounds of commercially available technical grade urea was placed in a 4,000 gallon stainless steel reactor and heated until molten and thereafter at 155° C. as in the reactor of Example 1. A recovered product of 18,204 pounds had the following analysis: urea 31.7%, biuret 43.1%, cyanuric acid 18.6%, triuret 6.6%. To the molten material as it exited the reactor was added 1,100 pounds of powdered seed material (less than 20 mesh) which had an analysis as follows: urea 0%, biuret 37.0%, cyanuric acid 60.1%, ammelide 2.9%. The recovered reactor product was crudely mixed with this seed material via a New Holland skid-loader. After a cooling period of five hours the product was sized through a combination jawcrusher and set of rolls to between 1 mesh and 4 mesh over a rotary-shaker screen. 15,600 pounds of this sized intermediate material was loaded into a vertical bed, forced air oven, wherein the bed dimensions were 12 feet by 11 feet and the bed depth was about 2.5 feet. The charged product was held in place by ¼ inch mild steel screen on two vertical faces of the oven bed. Heat was supplied to the product via a 13,000 cfm Twin City blower which pushed recycled air across a 300 KW duct heater. Over a four hour period the product bed temperature increased from 24° C. to 120° C. The product bed temperature was advanced 10° C. every two hours with a 3° C. plus or minus variation until reaching 180° C. The product was heated at 180° C. for an additional 24 hours, the total time in the oven being 40 hours. 9,160 pounds of final product with the following analysis was recovered: urea 0%, biuret 27.3%, cyanuric acid 67.5%, ammelide 5.2%.

EXAMPLE 6

200 grams of urea was heated in a stainless steel beaker at atmospheric pressure and after melting was progressively heated to 213° C. over a 35 minute period. 147 grams of intermediate material was recovered and had the following analysis: urea 38.8%, biuret 29.9%, cyanuric acid 30.2%, ammelide 1.1%. This product was cooled to 23° C. over a one hour period, sized between 4 and 16 mesh, and placed in a stainless steel pan at a bed depth of one inch. The product was heated in a Faberware convection oven at 193° C. for 20 hours. The particles retained their individual shapes and there was no fusion between particles or to the pan surface. 103 grams of final product was recovered which had the following analysis: urea 12.4%, biuret 13.2%, cyanuric acid 70.5%, ammelide 3.9%.

EXAMPLE 7

A charge of 45,600 pounds of intermediate material was prepared as in Example 1, and had an analysis of urea 33.4%, cyanuric acid 20.7%, biuret 41.8%, triuret 4.1%. This material was loaded into a horizontal tray, forced air oven wherein the tray dimensions were 18 feet by 12 feet and the product bed depth was 50 inches. Recycled air, heated by a 180 KW duct heater, was circulated upwardly through the product bed by a 26,000 cfm Twin City blower. Evolving ammonia was captured in water. The product was taken progressively from 25° C. to 110° C. over a four hour period. Thereafter the product bed temperature was gradually increased to 127° C. over a 14 hour period and held at this temperature for an additional 18 hours, the total elapsed time being 36 hours. The product recovered from this heating step was slightly fused together so as to form two large blocks and had an analysis as follows: urea 15.1%, biuret 55.1%, cyanuric acid 25.7%, triuret 4.1%. 42,408 pounds of product were recovered. 1,000 pounds of this material was sized between 2 and 16 mesh and loaded into a horizontal tray, forced air oven with a bed area of 16 square feet and a bed depth of 12 inches. The product was heated at 166° C. for 35 hours with a horizontal air sweep of about 1500 cfm. Recovered product totaled 749 pounds and had the following analysis: urea 0%, cyanuric acid 60.1%, biuret 37.0%, ammelide 2.9%. The product remained free flowing at all times during heating and did not adhere to any metal surfaces of the oven.

EXAMPLE 8

200 grams of feedstock material with an analysis of 34.3% urea, 18.0% cyanuric acid, 43.1% biuret, and 4.6 triuret by weight was sized between 2 mesh and 4 mesh and placed in a stainless steel tray so that the product bed depth was ¾ inch. The tray was placed in a convection oven and heated to 140° C. during a one-half hour period. After an additional heating period of 65 hours at 140° C., the tray product was analyzed and found to contain 13.5% urea, 28.6% cyanuric acid, 53.2% biuret, and 4.7% triuret. 5 grams of this material was ground so that the particle size was between 20 mesh and 100 mesh and placed on a watchglass so that the product bed depth was ⅛ inch. The watchglass was then placed back into the convection oven and heated at 140° C. for 72 hours. The product which resulted from this final pyrolysis analyzed 3.3% urea, 37.5% cyanuric acid, 54.3% biuret, and 4.9% triuret. This example is illustrative of the process disclosed and claimed in Stephan et al U.S. Pat. No. 4,654,441 in which the purpose is to maximize the production of biuret, and here is illustrative of the fact that such process parameters do not produce a sufficiently high yield of cyanuric acid.

The following Table III shows the effect on the cyanuric acid content of the final reaction product of the second stage of the process of the present invention which results from varying the rate of increase of temperature in the course of the second stage of the process. The starting material for these examples was a first stage feedstock comprising 30% urea, 47% biuret, 15% cyanuric acid, and 8% triuret, with the product bed placed in the convection oven of Example I with a product bed depth of about 40 inches and a product particle mesh size of 1 to 4.

TABLE III

EXPECTED ANALYSIS (PERCENTAGE BY WEIGHT) FOR CYANURIC ACID (CA) DURING SECOND STAGE PYROLYSIS - UNDER VARIOUS HEATING PROGRAMS
HEATING PROGRAM
(degree C.)

| Time (hrs.) | Ex. 9 Temp. | % CA | Ex. 10 Temp. | % CA | Ex. 11 Temp. | % CA | Ex. 12 Temp. | % CA | Ex. 13 Temp. | % CA | Ex. 14 Temp. | % CA |
|---|---|---|---|---|---|---|---|---|---|---|---|---|
| 0 | 105 | 15 | 105 | 15 | 105 | 15 | 105 | 15 | 105 | 15 | 120 | 15 |
| 5 | 107 | 15 | 107 | 15 | 107 | 15 | 107 | 15 | 107 | 15 | 125 | 15 |
| 10 | 110 | 16 | 110 | 16 | 110 | 16 | 110 | 16 | 110 | 16 | 130 | 16 |
| 15 | 110 | 17 | 115 | 18 | 115 | 18 | 115 | 18 | 115 | 18 | 135 | 16 |
| 20 | 115 | 19 | 120 | 20 | 123 | 21 | 123 | 21 | 123 | 21 | 140 | 16 |
| 25 | 122 | 21 | 127 | 22 | 131 | 24 | 131 | 24 | 131 | 24 | 150 | 16 |
| 30 | 130 | 24 | 135 | 25 | 140 | 29 | 140 | 29 | 140 | 29 | 160 | 16 |
| 35 | 140 | 28 | 150 | 34 | 160 | 40 | 165 | 42 | 170 | 44 | | |
| 40 | 160 | 34 | 170 | 42 | 180 | 51 | 190 | 54 | 200 | 60 | | |
| 45 | 160 | 41 | 170 | 50 | 180 | 58 | 190 | 63 | 200 | 69 | | |
| 50 | 160 | 44 | 170 | 55 | 180 | 63 | 190 | 69 | 200 | 75 | | |
| 55 | 160 | 47 | 170 | 58 | 180 | 67 | 190 | 73 | 200 | 79 | | |
| 60 | 160 | 50 | 170 | 61 | 180 | 70 | 190 | 76 | 200 | 82 | | |
| 65 | 160 | 52 | 170 | 63 | 180 | 71 | 190 | 77 | 200 | 83 | | |
| 70 | 160 | 53 | 170 | 64 | 180 | 72 | 190 | 78 | 200 | 84 | | |

Examples 9 through 13 compositely show that, while starting at a temperature below the eutectic melting point, once the urea content is reduced and the biuret content is increased sufficiently to avoid the eutectic melting point range, further relatively rapid increase in temperature results in progressively higher cyanuric acid content in the second stage final product, with the cyanuric acid content being 53% at a final temperature of 160° C. (in Example 9), and with the cyanuric acid content being 84% at a final temperature of 200°, as in Example 13. Table III also illustrates in its Example 14 that, when starting with a second stage temperature above the eutectic melting point of the starting material, the proportion of cyanuric acid essentially does not increase. This occurs of course because of fusion of the product bed caused by the overheating and consequent melting of the reaction product at the beginning of the reaction, which results in a reduction in the exposed area of the reaction product so that the heated air does not circulate therethrough and ammonia cannot be released, which stops the conversion to cyanuric acid.

Thus, in sum, and presented with a given first stage reaction product acceptable for purposes of the present invention, the operational technique to achieve a desired cyanuric acid content in the final reaction product of the second stage of the process is that of determining the eutectic melting point of the second stage starting material at hand, initiating the heating of the second stage reaction at slightly below such eutectic melting point, then increasing the temperature of the reaction during the second stage of the process as fast as practical consistent with the proposition that the reaction should at all times be maintained near but continually below the melting point of the reaction product as it is then constituted.

As shown by the Tables I and II, tests indicate the softening temperature of the charge after the first phase actually goes up, with lower concentrations of urea and with increasing concentrations of biuret. With this in mind, when utilizing a first phase end product as a starting material for the second phase reaction, it is important in the second stage to initially heat at a sufficiently low temperature so tat melting of the charge does not occur. Example 14 of Table III demonstrates this. It is preferable to run the first phase of the process to the point where the urea content is as low as practicable and the biuret content is as high as practicable so that higher heating can occur initially or almost initially and can be increased faster in second place so that the second phase can be completed in a shorter time with a higher proportion of cyanuric acid in the final end product. This is the teaching of the Examples 9 through 13 of Table III, considered compositely. As a practical matter, for a commercial process, the major advantages of the process are realized using a feedstock containing less than about 30% urea and more than about 40% biuret by weight.

The data reflected by Table III were obtained at atmospheric pressure. Actually, under ambient conditions, during the second phase of the process there is a slight positive pressure in that an air sweep, i.e. forced circulation, is utilized to move scavenging air through the particulate reaction mass.

It will be understood that the foregoing examples are merely illustrative of the invention and that variations will readily occur to those skilled in the art to which the invention is addressed as to the equipment and processing conditions under which pyrolysis reactions characteristic of the present invention proceed, within the scope of the following claims.

What is claimed is:

1. A process in which urea is pyrolytically converted to cyanuric acid, said process comprising heating, in dry, particulate, and essentially solid state, a partially pyrolyzed reaction product containing less than about 40% urea by weight an at least from about 30% biuret by weight, the heating of such feedstock occurring while maintaining the particles in essentially solid phase and at a temperature substantially at or slightly below the softening temperature of the particles with forced hot gas flow interstitially through the particles for a sufficient time to increase the cyanuric acid content thereof until the reaction product is principally cyanuric acid, partly by conversion of urea to biuret and in turn by conversion of biuret to cyanuric acid.

2. The process of claim 1, comprising heating the particles at a temperature of between 100° C. to 200° C.

3. The process of claim 1, comprising heating the particulate reaction product with forced air circulation herethrough for a time sufficient to product a cyanuric acid content greater than about 70% by weight.

4. The process of claim 3, wherein the particle size of the feedstock is about 1 mesh or less.

5. The process of claim 3, wherein the particle size of the feedstock is in the range of about 4 mesh to about 16 mesh.

6. The process according to claim 3, comprising arranging the particulate feedstock in a bed to a depth of up to about 5 feet, and causing forced air circulation vertically or horizontally therethrough.

7. The process of claim 1, wherein the partially pyrolyzed reaction product comprising the feedstock for the process is prepared by subjecting urea to a pyrolyzation for a time and temperature, in generally inverse reaction, of between about 15 minutes at about 220° C. and about 24 hours at about 135° C., followed by cooling of the resulting partially pyrolyzed reaction product to solid form, and by comminuting same.

8. The process of claim 7, comprising promoting crystallization and accelerating cooling of the partially pyrolyzed reaction product by adding thereto a seed material in powder form.

9. The process of pyrolytically producing from urea a reaction product which is predominantly cyanuric acid without use of solvents or catalysts, said process comprising heating molten urea for a time and at a temperature to convert the urea to an intermediate reaction product comprising less than about 40% urea and at least about 30% biuret by weight, cooling and comminuting such intermediate reaction product, passing hot gas through the comminuted product at progressively increasing temperatures maintained near but below the melting point of the product so that the product is maintained in essentially solid phase, and continuing such heating of the product until the cyanuric acid content thereof is at least about 50% by weight.

10. The process of claim 9, wherein the heating of the molten urea is under conditions resulting in an intermediate realistic product comprising less than about 30% urea and at least about 40% biuret by weight.

11. The process of claim 10, comprising continuing the solid phase heating of the product until the cyanuric acid content thereof is at least about 70% by weight.

12. The process of claim 9, comprising continuing the solid phase heating of the product until the cyanuric acid content thereof is at least about 70% by weight.

* * * * *